United States Patent [19]

Hayashi et al.

[11] Patent Number: 5,314,488

[45] Date of Patent: May 24, 1994

[54] ACETABULAR SOCKET FOR AN ARTIFICIAL HIP JOINT

[75] Inventors: Kazuo Hayashi, Fukuoka; Noriyuki Ishida, Kyoto, both of Japan

[73] Assignee: Kyocera Corporation, Kyoto, Japan

[21] Appl. No.: 939,552

[22] Filed: Sep. 1, 1992

Related U.S. Application Data

[63] Continuation of Ser. No. 633,250, Dec. 21, 1990, abandoned.

[30] Foreign Application Priority Data

Dec. 27, 1989 [JP] Japan .................................. 1-341590

[51] Int. Cl.⁵ .............................................. A61F 2/34
[52] U.S. Cl. ........................................................ 623/22
[58] Field of Search .......................... 623/16, 18, 22, 23

[56] References Cited

U.S. PATENT DOCUMENTS

| | | | |
|---|---|---|---|
| 4,101,985 | 7/1978 | Baumann et al. | 623/22 |
| 4,662,891 | 5/1987 | Noiles | 623/22 |
| 4,801,300 | 1/1989 | Kurze et al. | 623/22 |
| 4,883,491 | 11/1989 | Mallory et al. | 623/22 |

FOREIGN PATENT DOCUMENTS 649913  6/1985  Switzerland .................... 623/22

*Primary Examiner*—Randall L. Green
*Assistant Examiner*—Mary Beth Jones
*Attorney, Agent, or Firm*—Spensley Horn Jubas & Lubitz

[57] ABSTRACT

An acetabular socket of an artificial hip joint including an acetabular socket, a stem and a stem head, wherein the acetabular socket takes a form of a virtually inverted bowl-shaped shell or a hemispherical shell as a whole, the opening edge of the socket has outer flanges at regular intervals along the circumference thereof, and the outer flange has vertical and horizontal concave grooves on the surface thereof.

With this acetabular socket, the outer flanges provided along the opening edge and the vertical and horizontal concave grooves provided on the outer flanges increase the contact area between the socket and the cortex bone, thereby raising the strength for supporting the acetabular socket.

This disclosure also includes an acetabular socket, wherein a coating layer comprised of living body activation material, such as apatite, is coated on the outer flanges and the shell of the acetabular socket.

2 Claims, 3 Drawing Sheets

ACETABULAR SOCKET FOR AN ARTIFICIAL HIP JOINT

This is a continuation of application Ser. No. 633,250 filed on Dec. 21, 1990, now abandoned.

BACKGROUND OF THE INVENTION

1. Field of the Invention

The present invention relates to an acetabular socket (shell) for an artificial hip joint.

2. Prior Art

As shown in FIG. 1, an artificial hip joint comprises artificial members used to replace and restore a hip joint located between an acetabular bone H and a femur F. An acetabular socket A is fitted and seated in a concave socket receiving section R provided in the acetabular bone H. A stem head SH provided at the upper end of a stem S embedded in a canal of the femur F is rotatably fitted in the above-mentioned acetabular socket A via a seat C made of high-density polyethylene. The acetabular socket A, stem head SH, and stem S are made of materials non-harmless to a living body, either of metal such as titanium, titanium alloy, or cobalt-chromium alloy, or of ceramics such as alumina ceramics or zirconia ceramics. The acetabular socket A is fitted in and secured to the concave socket receiving section R of the femur F to rotatably support the stem head SH. The socket is positioned at the interface between the living body and the artificial member and plays a very important role in receiving the dynamic load applied to the femur F. The conventional-type acetabular socket A takes a form of an inverted bowl-shaped shell or a hemispherical shell, is fitted in the concave socket receiving section R, and secured to the acetabular bone H by using screws B as shown in FIG. 6. This conventional type has the following problems:

(i) Referring to FIG. 7, a cortex bone H1 located on the normal acetabular bone H is a hard layer and a cancellous bone H2 inside the cortex bone H1 is a soft layer. The former can support external force, but the latter cannot. In the case of the conventional type, since the opening edge a1 (see FIG. 2) of the acetabular socket A is on the hemispherical surface of the socket A, the main area of the socket A contacts the cancellous bone H2 under pressure as shown in FIG. 6. In addition, since the opening edge a1 does not contact the cortex bone H11 which functions as an opening edge a1 of the concave socket receiving section R, the area of the cortex bone H1 for sturdily supporting the socket A is insufficient.

(ii) Another problem with artificial hip joint is that, with the passage of time, the acetabular socket A gradually sinks into the acetabular bone H (what is called "migration") due to repeated hip joint movement and the effect of powder generated during such movement. This hinders the normal function of the hip joint or causes stress concentration at the hip joint, inducing secondary disease. One of the causes of this problem is the fact that the opening edge a1 has no structural relation to the cortex bone H11.

SUMMARY OF THE INVENTION

The object of the present invention is to solve the above-mentioned problems encountered in the prior art.

More particularly, the present invention provides an artificial hip joint comprising evenly spaced, outward slanting flanges or braces along the circumference of the opening edge of an inverted bowl-shaped shell or a hemispherical shell, wherein said flanges are characterized by vertical and horizontal concave grooves, thereby increasing the contact area between the socket and the cortex bone to (a) increase strength for supporting the acetabular socket, (b) hinder migration, and (c) prevent the socket from rotating or tilting.

DETAILED DESCRIPTION OF THE INVENTION

Figure 1:
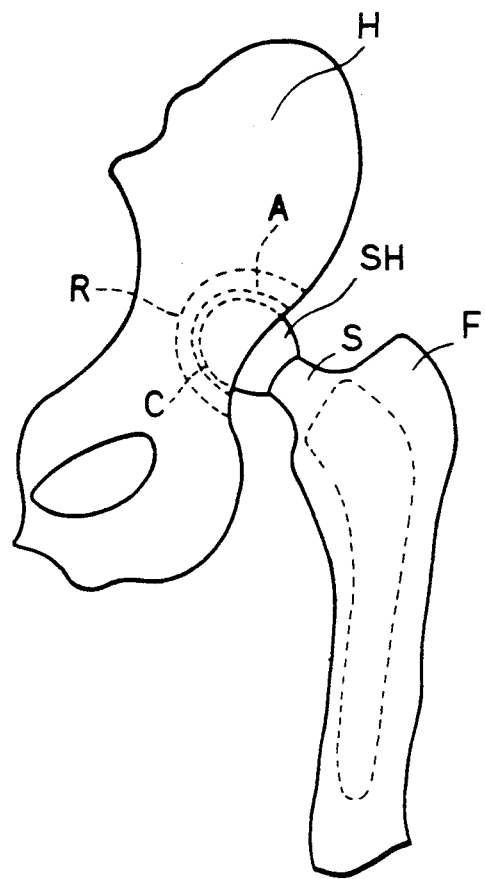
FIG. 1 is an overall view illustrating an artificial hip joint in which the acetabular socket of the present invention is incorporated.
Figure 2:
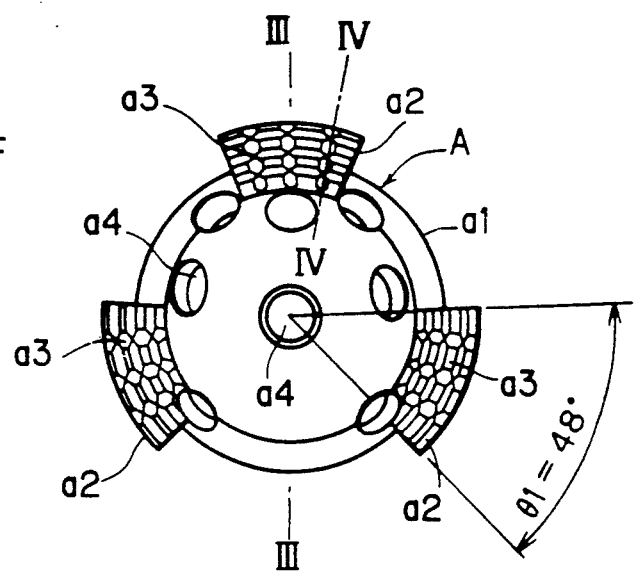
FIG. 2 is a plan view illustrating a first embodiment of the acetabular socket of the present invention.
Figure 3:
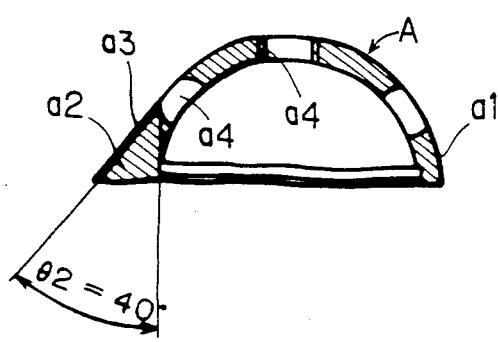
FIG. 3 is a sectional view taken on line III—III of FIG. 2.
Figure 4:
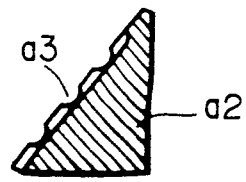
FIG. 4 is a sectional view taken on line IV—IV of FIG. 2.

The structure of a preferred embodiment of the present invention is detailed below referring to FIGS. 2 and 3. The acetabular socket A takes a form of a virtually inverted bowl-shaped shell or a hemispherical shell as a whole, the opening edge a1 of the socket has outer flanges or braces a2 at regular intervals along the circumference thereof, and the outer flange a2 has vertical and horizontal concave grooves a3 on the surface thereof. In the case of the preferred embodiment, the outer flange a2 has a flat arc shape and its thickness is greater at its lower section. The outer flanges a2 are provided along the circumference of the opening edge a1 at intervals of about 120°. Code a4 represents a screw hole.

Figure 5:
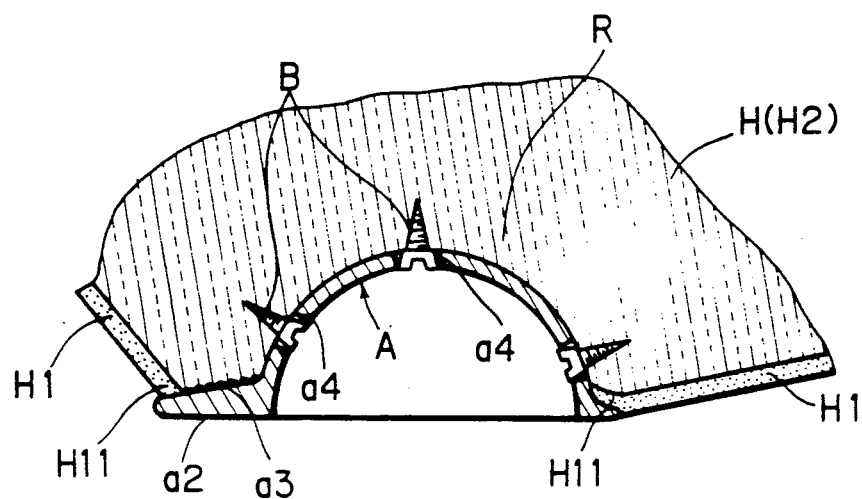
FIG. 5 is a sectional view illustrating how the main section of the acetabular socket of the present invention is secured to an acetabular bone.
Figure 6:
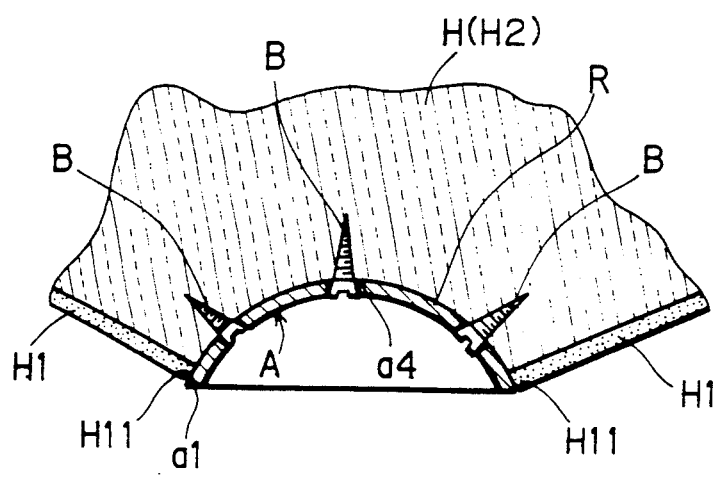
FIG. 6 is a view similar to FIG. 5 showing the conventional acetabular socket.
Figure 7:
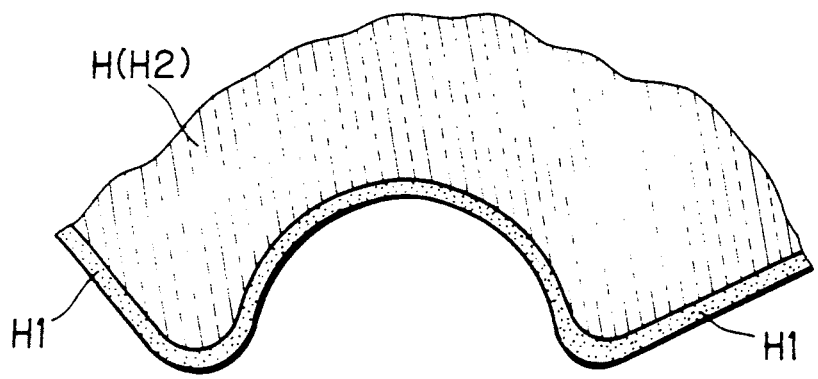
FIG. 7 is a sectional view illustrating the main section of a normal acetabular bone.

The operating principle and function of the acetabular socket A having the above-mentioned structure are detailed below. A method for securing the acetabular socket A to the acetabular bone H is the same as that required for the conventional type. As shown in FIG. 5, the socket A is fit in and secured to the concave socket receiving section R by using screws B. Since the acetabular socket A of the present invention has the outer flanges a2 provided at regular intervals along the circumference of the opening edge a1 at the outer flanges a2 are installed to cover the opening edge of the concave socket receiving section R and the cortex bone H11 of the acetabular bone H. Therefore, the outer flanges a2 and the cortex bone H11 that closely contact the outer flanges a2 behind are used to support the acetabular socket A, thereby making the hard area for supporting the acetabular socket A larger than that of the conventional type and raising resistance against the load applied from the stem head SH to the socket A. The outer flanges a2 also greatly increase the resistance of the acetabular socket A against rotating and tilting. Furthermore, the outer flange a2 has a shape of a flat arc as shown in FIG. 2 to provide higher adaptability to the shape of the mating acetabular bone H and the thickness of the flange is made greater at its lower section for higher reinforcement and rigidity in the direction of the opening edge a1. Moreover, the vertical and horizontal concave grooves a3 are formed on the outer flanges a2 to increase the areas of the flanges for contacting the cortex bone H11, thereby raising the close contact performance at the interface of the bone. As an additional special advantage, the outer flange a2 extended slantly from the inverted bowl-shaped shell or hemispherical shell engages with the cortex bone H11 and prevents the acetabular socket A from gradually moving upward to the acetabular bone H even after the use of the socket A for an extended period of time, thereby preventing migration.

EMBODIMENT 1

In the figures of the preferred embodiment, three outer flanges a2 are provided at intervals of about 120° along the circumference of the opening edge a1. The arc angle $\theta1$ of the outer flange a2 is 48° as shown in FIG. 2. The thickness of the outer flange a2 is made greater at its lower section by setting the extension angle $\theta2$ of the flange to about 40° as shown in FIG. 3. The extension length of the outer flange a2 is desired to be 2 to 10 mm. In addition, a coating layer (not shown) made of living body activation material, such as apatite, is coated on the outer flanges a2 and the inverted bowl-shaped shell or hemispherical shell of the acetabular socket A to promote proper and secure connection to the bones. The depth of the vertical and horizontal concave groove a3 is about 0.75 mm and the acetabular socket A is made of titanium alloy (Ti-6Al-4V).

The above embodiment of the present invention is just only one example. It is apparent that other embodiments of the invention are possible depending on the case of a disease.

EMBODIMENT 2

Figure 8:
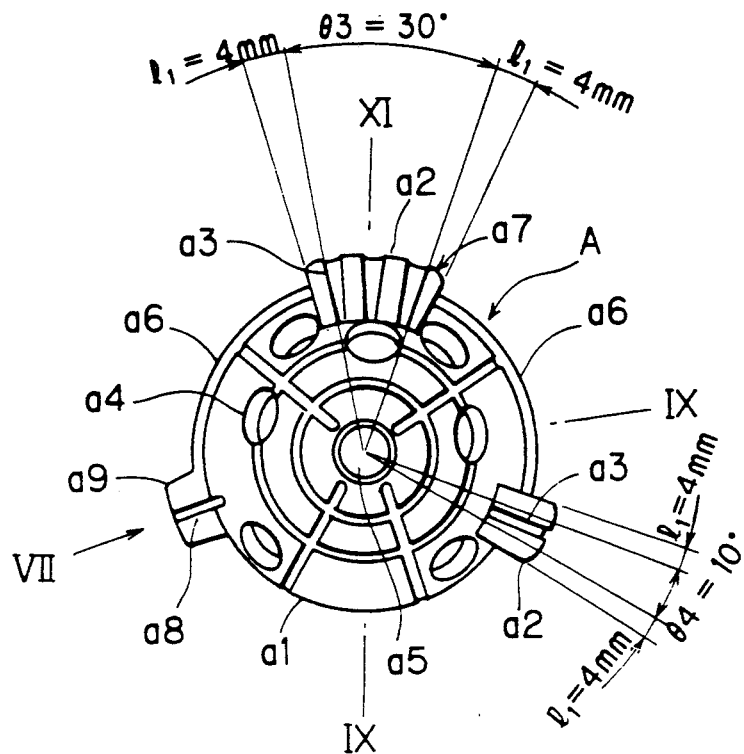
FIG. 8 is a plan view illustrating the second embodiment of the acetabular socket of the present invention.
Figure 9:
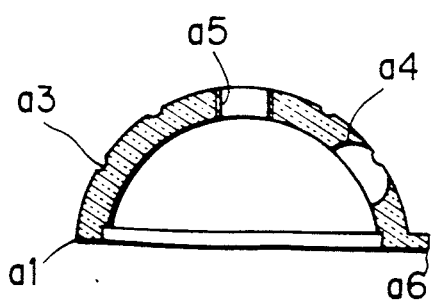
FIG. 9 is a sectional view taken on line IX—IX of FIG. 8.
Figure 10:
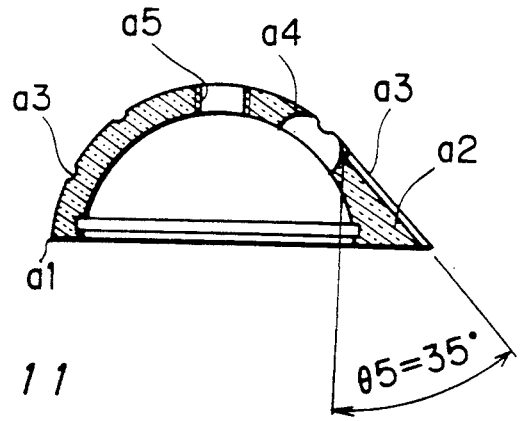
FIG. 10 is a sectional view taken on line IX—IX of FIG. 8.
Figure 11:
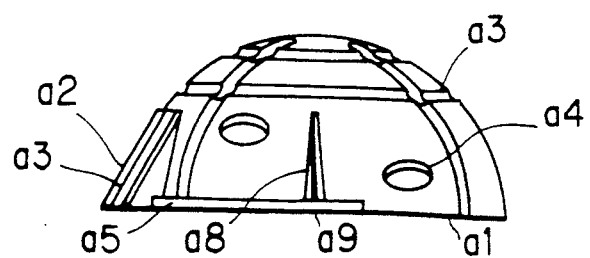
FIG. 11 is a view taken in the direction of arrow VII of FIG. 8.

FIG. 8 shows another embodiment of the present invention applicable when the amount of the acetabular bone H is insufficient. The outer flanges a2 are provided about 105° apart from each other and are relatively small as compared with those of the first embodiment. The shape of the outer flange a2 is determined by its arc angle ($\theta3$ or $\theta4$) and its width $l_1$. In the case of this embodiment, $\theta3=30°$, $\theta4=10°$ and $l_1=4$ mm. The thickness of the outer flange a2 is made greater at its lower section by setting the extension angle $\theta5$ to 35° as shown in FIG. 10. If large outer flanges a2 are used when the amount of the acetabular bone H is insufficient, the acetabular bone is required to be cut excessively, causing adverse effect to the strength of the acetabulum bone H. In such an occasion, the acetabulum socket having smaller outer flanges may be used. In the second embodiment, in addition to the two outer flanges a2, a rotation prevention beam or a plate-like rib member a8 and an extension or a radial web a9 are provided along the circumference of the opening edge a1, 105° away from the outer flanges a2 that have an arc angle of $\theta3=30°$. The acetabular socket of the second embodiment has further advantages in actual medical operations. Actual medical operation methods for artificial hip joints are classified into two types. In the case of the first method, the trochanter of the femur is cut off and replaced. In the case of the second method, the trochanter is replaced without cutting it off. The latter method has many advantages; the amount of bleeding is scarce during operation, operation time is shorter, trochanter installation is not necessary, and nonunion and other problems are not caused after operation. However, the method also has disadvantages. The visual field is limited during operation and it is well known that cutting the acetabular bone H without cutting off the trochanter is much more difficult than that with cutting off the trochanter. Since the acetabular socket of the first embodiment of the present invention has the outer flanges a2, which are relatively large it is desirable that replacement should be done after cutting off the trochanter. When the trochanter is not desired to be cut off, however, an acetabulum socket in accordance with the second embodiment may be used. Although the acetabulum socket of the second embodiment has relatively small outer flanges, the rotation prevention beam a8 and the extension a9 are used effectively to prevent the rotation and migration of the acetabulum socket. Furthermore, since the rotation prevention beam a8 is sufficiently narrower than the outer flange a2, cutting-off operation to the acetabular bone can be done easily even when the trochanter is existing. This embodiment also has generally planar projections or beam members a6 provided at the opening edge of the acetabular socket, having 0.5 to 3 mm in thickness and 1 to 5 mm extended from the spherical surface. Even if migration occurs after the acetabular socket A was installed in the acetabular bone H and used for an extended period of time, this projection a6 can prevent migration from advancing. The corner section of the outer flange a2 of this embodiment is rounded to have a round shape a7 as shown in FIG. 8. It is desirable that the radius of the round shape a7 should be $l_1=4$ mm in width. This makes replacement to the acetabular bone easier. Code a5 represents a screw hole. This screw hole is provided to install an apparatus that is used to drive the acetabular socket A into the acetabular bone H.

As described above, in the case of the present invention, the outer flanges are provided at regular intervals along the circumference of the opening edge of the acetabular socket to increase the contact area of the socket to the cortex bone, thereby raising the strength for supporting the acetabular socket, preventing the socket from rotating or tilting. Accordingly, the embodiment has significant advantages in greatly improving the performance of the conventional artificial hip joint.

We claim:
1. An artificial acetabulum socket for an artificial hip joint comprising:
   a generally hemispherical shell having an opening edge;
   a plurality of outer flanges along the circumference of said opening edge;
   at least one generally planar beam member provided in proximity to said opening edge and extending between said flanges;
   a plate-like rib member for increasing resistance against rotational movement of said acetabulum socket; and
   a radial web extending radially in proximity to said opening edge, wherein said plate-like rib member is provided on said radial web and extends along the external surface of said hemispherical shell.

2. An artificial acetabulum socket for an artificial hip joint comprising:
- a generally hemispherical shell having vertical and horizontal grooves in the surface thereof and a plurality of screw holes, said shell defining an opening for receiving a stem head;
- a plurality of arcuate flanges along the circumference of an opening edge of said hemispherical shell at regular intervals and extending radially from the exterior of the shell and oriented transverse to the shell opening wherein each flange has a generally flat bottom surface along the shell opening and a slanted bearing surface angled at a predetermined angle with respect to said bottom surface to define a generally wedge-shaped cross-section, wherein said predetermined angle is approximately 35°, and wherein a first of said arcuate flanges extends along the periphery of said hemispherical shell at an arc angle of 30° and a second of said arcuate flanges extends along the periphery of said hemispherical shell at an arc angle of 10°; and
- at least one arcuate generally planar beam member extending between said arcuate flanges in proximity to said opening edge.

* * * * *